United States Patent

Sanazaro

(10) Patent No.: US 9,205,164 B2
(45) Date of Patent: Dec. 8, 2015

(54) SCENT-EMITTING ARROWHEAD

(71) Applicant: Daniel Sanazaro, Cuba, MO (US)

(72) Inventor: Daniel Sanazaro, Cuba, MO (US)

(*) Notice: Subject to any disclaimer, the term of this patent is extended or adjusted under 35 U.S.C. 154(b) by 0 days.

(21) Appl. No.: 14/244,013

(22) Filed: Apr. 3, 2014

(65) Prior Publication Data

US 2015/0018142 A1    Jan. 15, 2015

Related U.S. Application Data

(60) Provisional application No. 61/845,218, filed on Jul. 11, 2013.

(51) Int. Cl.
| | |
|---|---|
| F42B 6/08 | (2006.01) |
| A61L 9/12 | (2006.01) |
| F42B 12/36 | (2006.01) |
| F42B 12/38 | (2006.01) |
| F42B 12/46 | (2006.01) |
| F42B 12/40 | (2006.01) |

(52) U.S. Cl.
CPC ... *A61L 9/12* (2013.01); *F42B 6/08* (2013.01); *F42B 12/362* (2013.01); *F42B 12/38* (2013.01); *F42B 12/46* (2013.01); *F42B 12/40* (2013.01)

(58) Field of Classification Search
CPC ............. F42B 6/04; F42B 6/08; F42B 12/362
See application file for complete search history.

(56) References Cited

U.S. PATENT DOCUMENTS

| | | | | |
|---|---|---|---|---|
| 4,881,743 A | * | 11/1989 | Fiorenzo | 473/577 |
| 5,035,435 A | | 7/1991 | Burgeson et al. | |
| 5,164,178 A | * | 11/1992 | Muysson | 424/76.4 |
| 5,836,842 A | * | 11/1998 | McLearan | 473/581 |
| 6,174,251 B1 | | 1/2001 | Lemote | |
| 6,450,905 B1 | * | 9/2002 | Edlund | 473/581 |
| 8,439,777 B2 | | 5/2013 | Pierce et al. | |
| 8,444,512 B2 | | 5/2013 | Pierce et al. | |
| 2008/0051231 A1 | | 2/2008 | Everett | |
| 2013/0065716 A1 | | 3/2013 | Pierce et al. | |

* cited by examiner

*Primary Examiner* — John Ricci
(74) *Attorney, Agent, or Firm* — Daniel Boudwin; Global Intellectual Property Agency LLC

(57) ABSTRACT

Described is a scent-emitting arrowhead comprising a hollow container having a first end, a second end, and an interior cavity. The interior cavity is adapted to receive and store a scent-emitting material. The container further comprises a plurality of vents that allow the scent-emitting material to be dispersed into the surroundings during the arrow's flight. The first end of the container is adapted to attach to the shaft of an arrow, and the second end of the container comprises a removable lid adapted to removably attach to the second end of the container. The lid is substantially conical in shape such that the lid defines the tip of the arrowhead. The vents may be covered by one or more removable adhesive strips that prevent the scent-emitting material from escaping through the vents until the time when the arrowhead is desired to be used.

9 Claims, 3 Drawing Sheets

SCENT-EMITTING ARROWHEAD

CROSS REFERENCE TO RELATED APPLICATION

This application claims the benefit of U.S. Provisional Application No. 61/845,218 filed on Jul. 11, 2013, entitled "In-Flight Scent Dispenser." The above identified patent application is herein incorporated by reference in its entirety to provide continuity of disclosure.

BACKGROUND OF THE INVENTION

Field of the Invention

The present invention relates to arrowheads. More specifically, the present invention relates to a scent-emitting arrowhead comprising a tubular container having a first end, a second end, and an interior cavity. The interior cavity is adapted to receive and store scent-emitting materials. The container comprises a plurality of vents that allow the scent-emitting material to disperse into the surroundings when the arrow is in flight. The first end of the container is adapted to attach to the shaft of an arrow, while the second end of the container comprises a removable lid that provides access to the interior cavity of the container.

Hunters commonly use scented materials to attract or lure animals towards a hunting stand. Scent-drenched rags may be deposited in proximity to a hunting stand to achieve this effect. However, the need for a hunter to carry and place the scent-drenched rag may result in the rag carrying the hunter's scent which may deter animals from approaching the scent-drenched rag. Further, animals distant to the hunting stand may not be close enough to be drawn by the scented material, and a hunter may not be able to disperse the smell to attract the animal without scaring the animal away. Similarly, the wind may scatter deposited scents, and hunters may not be able to reapply a new scent without disturbing any nearby animals.

Devices are known in the prior art that describe hunting arrows that are adapted to disperse scents. Such devices comprise an arrow having an internal cavity in which a lure or other attractant can be deposited. The scented material is contained within the cavity until the arrow contacts a target, at which time the scented material is released. Thus, the scent is only released when the arrow strikes a target and is held within the arrowhead until that time.

The present invention describes a scent-emitting arrowhead comprising a container having an internal cavity and a removable lid. The container comprises a plurality of vents that allow scented material deposited within the internal cavity to escape the container. The first end of the container is adapted to attach to an arrow in the same manner as a traditional arrowhead. The removable lid is positioned at the second end of the container and provides access to the internal cavity of the container. The removable lid also serves as the tip of the arrowhead. Once the arrowhead is attached to an arrow, a hunter may deposit any lure desired into the internal cavity of the container and secure the container with the removable lid. The vents may be covered by a removable adhesive strip until the time when the arrow head is to be used. The hunter is then able to shoot an arrow having the scent-emitting arrowhead in the usual manner. As the arrow flies through the air, the scent or lure container therein will be dispersed throughout the arrow's flight.

DESCRIPTION OF THE PRIOR ART

Devices have been disclosed in the prior art that relate to arrowheads. These include devices that have been patented and published in patent application publications. These devices generally relate to scent-emitting devices for use with arrows. The following is a list of devices deemed most relevant to the present disclosure, which are herein described for the purposes of highlighting and differentiating the unique aspects of the present invention, and further highlighting the drawbacks existing in the prior art.

One such device exemplifying the art is U.S. Pat. No. 5,035,435 to Burgeson et al. entitled "Arrow Mounted Scent Carrier," which discloses a scent-emitting device comprising a carrier composed of absorbent, porous material. The carrier is sized so that it may be attached to the shaft of an arrow. The carrier can be removably secured adjacent to the fletching or feathered end of an arrow and is saturated with the desired scent. In operation, a user shoots the arrow in a high arc so that the arrow lands in an upright position such that the head of the arrow becomes embedded in the ground. Burgeson et al. does not disclose a scent-emitting arrowhead and instead discloses a carrier that can be secured to the lower end of the shaft of an arrow. Further, Burgeson uses an absorbent material that can be saturated with a liquid scent formulation which will disperse in the wind once the arrow comprising the scent carrier is embedded in the ground.

U.S. Pat. No. 6,174,251 to Lemote entitled "Arrow for Dispersing Olfactant" discloses an arrow having an interior cavity in which a breakable container, a means for breaking the container, and a wick are positioned. The breakable container is designed to rupture upon the arrow's impact with a target, and the container is designed to remain intact during the flight of the arrow. Once the container ruptures, the wick absorbs scented liquid released from the container, and gas produced by evaporation of the liquid on the wick is released into the surroundings through apertures on the walls of the arrow. Thus, Lemote does not disclose an arrowhead but instead discloses an arrow having an internal cavity in which a container used to store scented liquid is positioned. Further, the scent is only released upon impact of the arrow with a target, which results in the container rupturing and release of the liquid contained therein.

U.S. Pat. No. 8,444,512 to Pierce et al. entitled "Scent Dispersing Apparatus" discloses a breakable housing containing scented liquid that can be attached to an arrow and that breaks upon contact with a target. The housing further comprises several large fins about the periphery of the housing so as to prevent the housing from being embedded in the soil. Thus, Pierce does not disclose an arrowhead having a plurality of vents that allow the scented material to be dispersed throughout the flight of the arrow, and instead discloses a breakable container that releases the scented material upon impact of the arrow with a target.

U.S. Pat. No. 8,439,777 to Pierce et al. entitled "Scent Dispersing Apparatus" discloses an attachment for an arrow comprising an enclosure in which a breakable capsule containing scented material can be placed. The attachment further comprises a plunger that moves slidably inside the enclosure that is adapted to rupture the capsule when the plunger impacts a solid surface. Once ruptured, the liquid within the capsule escapes the capsule through cutouts formed in the enclosure. Thus, Pierce discloses a device that releases scent only upon impact of the arrow with a target. Further, Pierce requires the use of a breakable container that holds liquid therein.

U.S. Patent Application Publication No. 2013/0065716 to Pierce et al. entitled "Frangible Payload Delivery Apparatus" discloses a scent dispersing arrowhead comprising a breakable hollow container that is able to deliver various payloads. The container is attached to a base having a threaded member adapted to engage with the threading of an arrow shaft. Several impact stanchions are attached to the perimeter of the container and are adapted to fracture the container upon impact of the arrow with a target. Thus, Pierce et al. does not disclose an arrowhead having an internal cavity adapted to store scented material which can be released throughout the flight of an arrow by means of vents disposed on the arrowhead. Instead, Pierce discloses a breakable container that stores scented material which is only released upon impact.

Finally, U.S. Patent Application Publication No. 2008/0051231 to Everett entitled "Scent Dispersing Arrow" discloses an arrow having a shaft that comprises a first and second part. The first and second parts are separable and enclose a chamber. The chamber comprises a plurality of holes in a portion of its wall which allow scent to disperse into the air. However, scent is only dispersed into the air when a solid scent stick moves within the chamber to a portion of the chamber having holes, which occurs when the arrow impacts the ground. Thus, Everett discloses an arrow adapted to release an animal attracting scent and that contains a chamber positioned within the shaft of the arrow that encloses a scented stick. Scent is only released upon impact of the arrow with the ground or other surface and is not released throughout flight. Everett does not disclose an arrowhead adapted to receive a scented material and that releases the material throughout flight through holes disposed on the arrowhead.

These prior art devices have several known drawbacks. Several devices discloses in the prior art disclose arrows adapted to release a scented material. Such devices require a hunter to carry a specially designed arrow in order to release animal attracting scents, which may be inconvenient or undesirable for a hunter. Other devices disclosed in the prior art include breakable containers designed to release animal attracting scents. Such devices suffer the drawback that no scent is released during the flight of the arrow, and scent is only released upon impact of the arrow with a target.

The present invention discloses an arrowhead comprising an interior cavity, a first end, and a second end. The first end comprises a means for attaching to the shaft of an arrow, while the second end comprises a removable lid allowing access to the interior cavity of the arrowhead. Scent-emitting material can be placed in the interior cavity and can be released during flight through vents disposed on the arrowhead. The vents may be covered by one or more removable adhesive strips until the time when the arrowhead is desired to be used. In this way, the arrowhead of the present invention deposits a line of scent along the flight path of the arrow, and animals may follow the line of scent towards the hunter.

In light of the devices disclosed in the prior art, it is submitted that the present invention substantially diverges in design elements from the prior art and consequently it is clear that there is a need in the art for an improvement to existing scent-emitting arrow or arrowhead devices. In this regard the instant invention substantially fulfills these needs.

SUMMARY OF THE INVENTION

In view of the foregoing disadvantages inherent in the known types of scent-emitting arrowheads now present in the prior art, the present invention provides a new scent-emitting arrowhead wherein the same can be utilized for providing convenience for the user when hunting animals and using scent-emitting materials to attract animals towards the hunter.

It is therefore an object of the present invention to provide a new and improved scent-emitting arrowhead that has all of the advantages of the prior art and none of the disadvantages.

It is another object of the present invention to provide a scent-emitting arrowhead that disperses an animal attracting scent throughout the flight of the arrow.

Another object of the present invention is to provide a scent-emitting arrowhead having a removable lid allowing a user access to the interior of the arrowhead so that the user can deposit any scent-emitting material desired.

Yet another object of the present invention is to provide a scent-emitting arrowhead that provides hunters with a means for dispersing animal attracting scents also dispersing human scent that may serve to deter animals from approaching.

Another object of the present invention is to provide a scent-emitting arrowhead that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
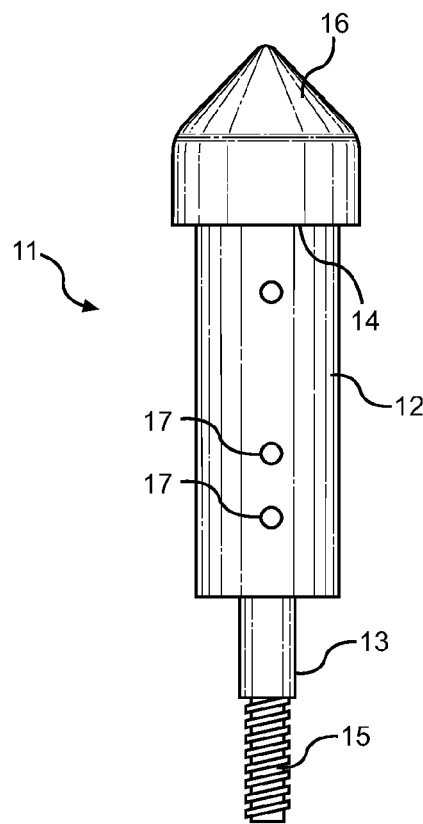
FIG. 1 shows a front view of the preferred embodiment of the scent-emitting arrowhead of the present invention.

Reference is made herein to the attached drawings. Like reference numerals are used throughout the drawings to depict like or similar elements of the scent-emitting arrowhead. For the purposes of presenting a brief and clear description of the present invention, the preferred embodiment will be discussed as used for attracting animals towards a hunting stand using a scent-emitting arrowhead that is able to disperse an animal-attracting scent throughout its flight. The figures are intended for representative purposes only and should not be considered to be limiting in any respect.

Referring now to FIG. 1, there is shown a front view of the preferred embodiment of the scent-emitting arrowhead of the present invention. The scent-emitting arrowhead 11 comprises a container 12 having a first end 13, an open second end 14, and an interior cavity. The interior cavity is adapted to receive and store scented materials or lures, particularly scented liquids. The first end 13 of the container 12 is adapted to attach to the shaft of an arrow. In the embodiment shown, the first end 13 comprises a threaded member 15 that is adapted to engage with the threaded interior of the shaft of an arrow. The second end 14 comprises a removable lid 16 that can be removed from the container 12 so as to allow access to the interior cavity of the container. Further, the removable lid 16 serves as the tip or leading end of the arrowhead. The container further comprises a plurality of vents 17 disposed on the side of the container 12. In the embodiment shown, the vents are circular apertures that are arranged in a single line extending from the first end 13 to the second end 14. However, other embodiments of the present invention may comprise a different number of vents or vents of other shapes. The vents allow the scented material to escape into the surroundings while an arrow having the arrowhead of the present invention is in flight. In the preferred embodiment, the vents are arranged in a single line such that when the interior cavity is filled with a scented liquid, the arrowhead can be oriented with the vents facing upwards to prevent the scented liquid from spilling out of the arrowhead prior to the arrow being shot.

Figure 2A:
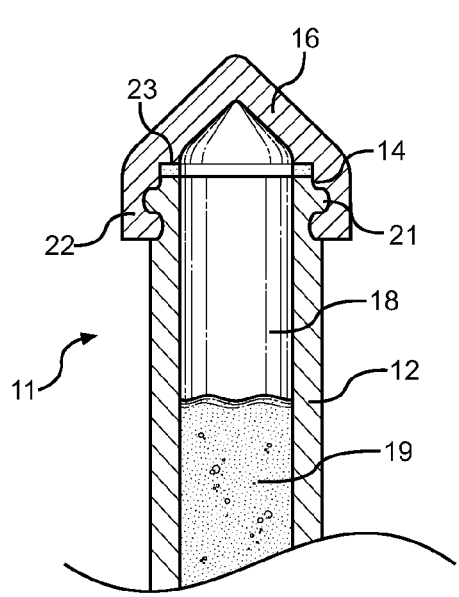
FIG. 2A shows a cross-sectional view of the preferred embodiment of the scent-emitting arrowhead of the present invention with the removable lid secured.
Figure 2B:
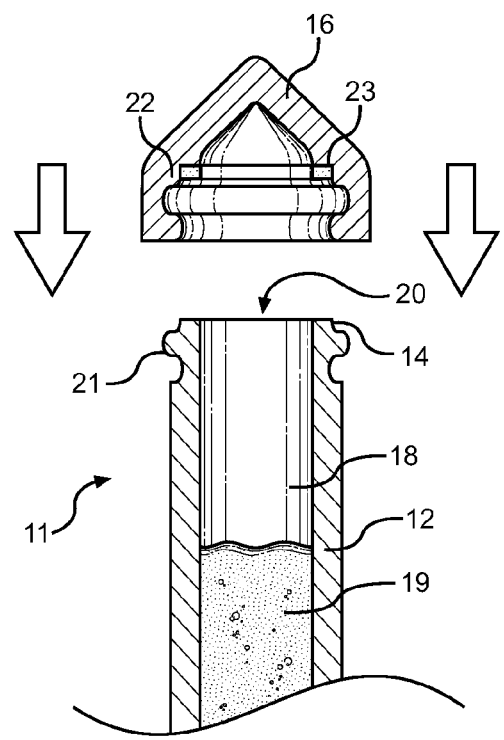
FIG. 2B shows a cross-sectional view of the preferred embodiment of the scent-emitting arrowhead of the present invention with the lid removed.

Referring now to FIGS. 2A and 2B, there is shown a sectional view of the preferred embodiment of the scent-emitting arrowhead of the present invention with the removable lid attached and removed, respectively. The scent-emitting arrowhead 11 comprises a container 12 having an interior cavity 18. The interior cavity 18 is adapted to receive and store scent-emitting material 19 or lures. Any type of scent-emitting material may be used, and the scent-emitting material may be in liquid form or solid form, such as a scented powder. A user may pour or load the scent-emitting material 19 into the interior cavity 18 through an opening 20 at the second end 14 of the container 12. A removable lid 16 is secured to the second end 14 of the container 12 and serves to enclose the interior cavity 18 such that the scent-emitting material 19 is held securely within the container 12.

In a preferred embodiment of the present invention, the removable lid 16 is attached to the second end 14 of the container 12 by means of a snap connection 21, 22. The lid 16 and the second end of the container 14 have snap connections 21, 22 that mate with one another so as to secure the removable lid 16 onto the container 12. The removable lid 16 further comprises an O-ring 23 such that when the lid 16 is placed on the container 12, a tight seal is created that secures the removable lid to the container and prevents any of the scent-emitting material 19 from escaping the container. In some embodiments of the invention, the removable lid attaches to the container by means of threading on the interior of the removable lid and on the exterior of the second end of the container.

Figure 3:
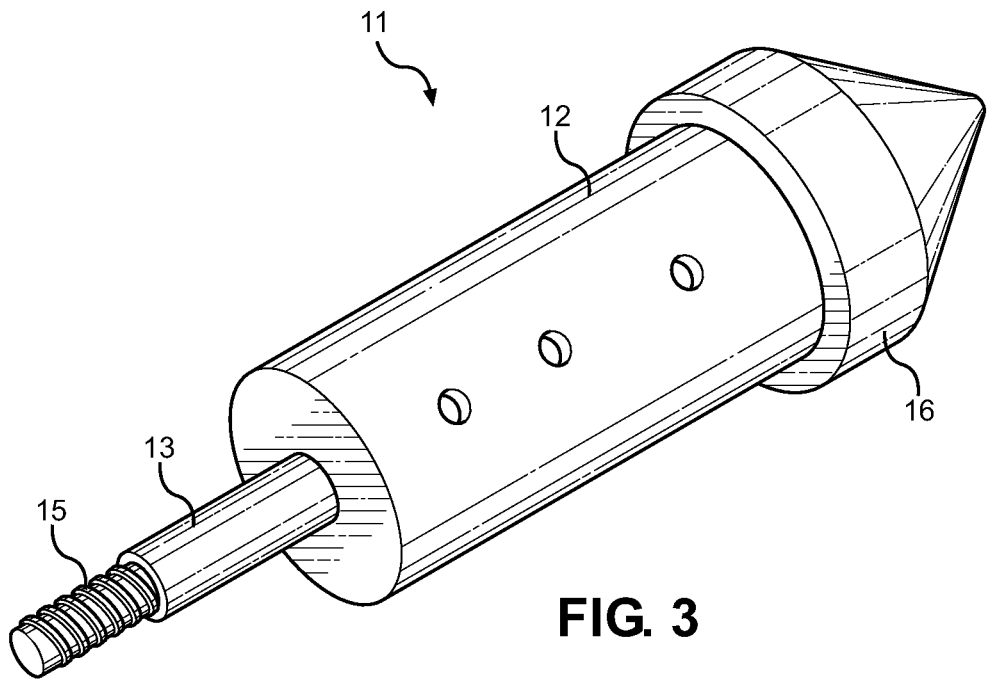
FIG. 3 shows a perspective view of the preferred embodiment of the present invention.

Referring now to FIG. 3, there is shown a perspective view of the scent-emitting arrowhead of the present invention. The container 12 is substantially tubular in shape. Further, the lid 16 is substantially conical in shape. In this way, the arrowhead is symmetrical and has an aerodynamic shape. Further, the first end 13 of the container 12 that has a threaded member 15 for connection to the shaft of an arrow is positioned in the center of the bottom face of the container 12. The central location of the threaded member allows the arrowhead to be positioned symmetrically about the shaft of the arrow, so as to provide an arrowhead having an aerodynamic shape.

Figure 4:
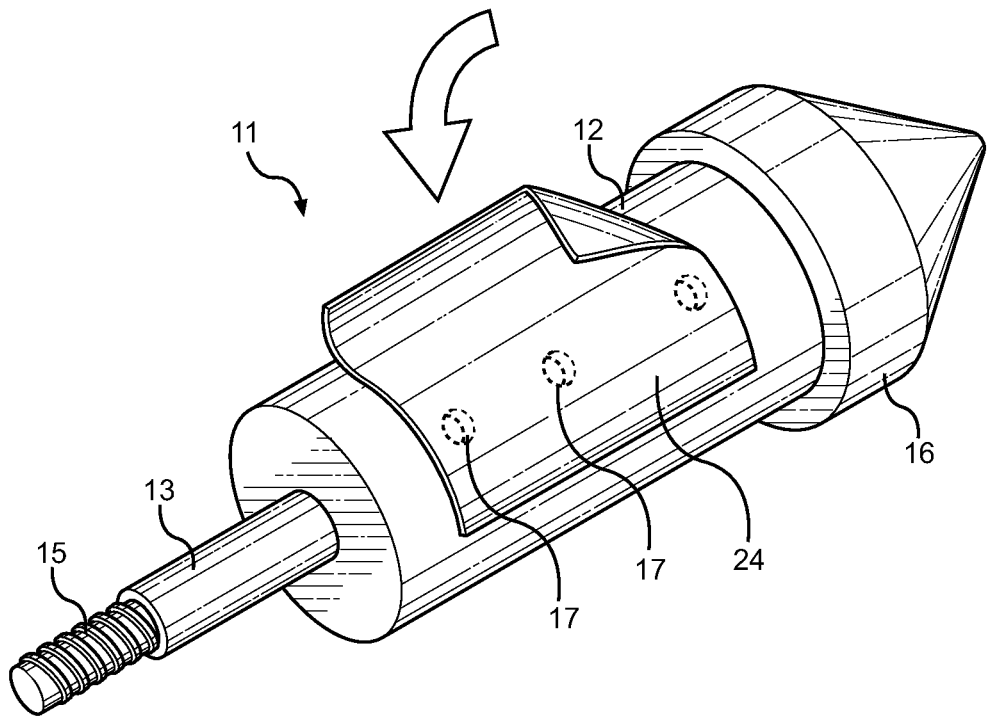
FIG. 4 shows an embodiment of the present invention having an adhesive strip used to cover the vents on the scent-emitting arrowhead.

Referring now to FIG. 4, there is shown an embodiment of the present invention having a removable adhesive strip covering the vents on the scent-emitting arrowhead. The scent-emitting arrowhead may include one or more removable adhesive strips 24 to cover the vents 17 until the arrowhead 11 is ready to be used. The removable adhesive strips 24 covering the vents 17 prevent the scented material placed in the interior cavity of the arrowhead from escaping through the vents until the time the arrowhead is desired to be used. When the arrowhead is ready to be used, the hunter may simply peel off the adhesive strips 24 so that the scented-material may escape the interior cavity of the arrowhead during flight.

In operation, a user attaches the first end 13 of the scent-emitting arrowhead 11 onto the shaft of an arrow. The user then removes the lid 16 exposing the opening at the second end of the container. The user may then deposit a scent-emitting material into the interior cavity of the container. For example, the user may pour a scented liquid into the interior cavity. The user may then reattach the removable lid by applying downward pressure sufficient to snap the lid 16 onto the container 12. Once the scent-emitting material is deposited in the container and the lid is secured onto the container, the user then removes the removable adhesive strips so as to expose the vents. Where scented liquid or a scented powder is used, the vents should be oriented upwards prior to peeling off the adhesive strips such that the scented liquid does not spill out of the container before the user shoots the arrow. The user is then able to shoot the arrow having the arrowhead of the present invention in the typical fashion, and throughout the flight of the arrow the scented material will escape the container through the vents disposed on the container leaving a trail of scent along the flight path of the arrow.

Figure 5:
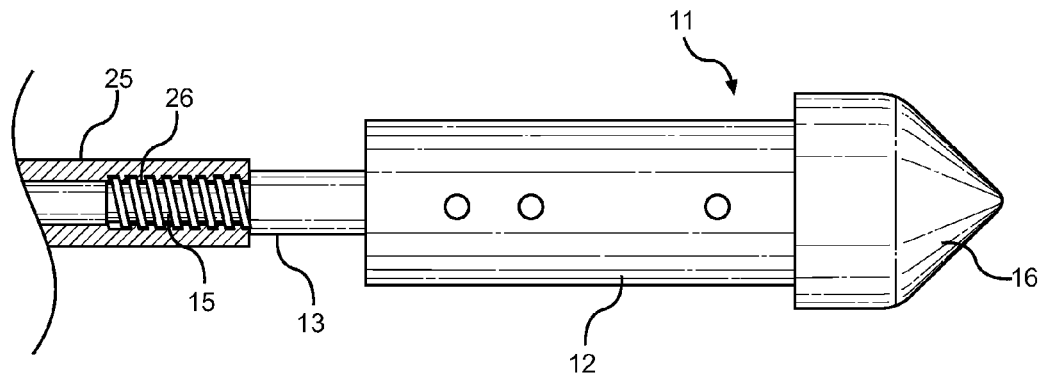
FIG. 5 shows a view of the scent-emitting arrowhead secured to the threaded shaft of an arrow.

Referring now to FIG. 5, there is shown a view of the scent-emitting arrowhead engaged with the shaft of an arrow. The shaft of an arrow 25 includes a threaded end 26 adapted to receive a threaded member 15 of an arrowhead. The preferred embodiment of the arrowhead of the present invention includes a threaded member 15 disposed at the first end 13 of the container 12. The threaded member 15 allows the arrowhead to be securely fastened to the shaft of an arrow. With the threaded member 15 secured to the shaft of an arrow 25, the removable lid 16 serves as the leading end or tip of the arrow, and provides an aerodynamic shape such that the arrow can be shot with accuracy.

Figure 6:
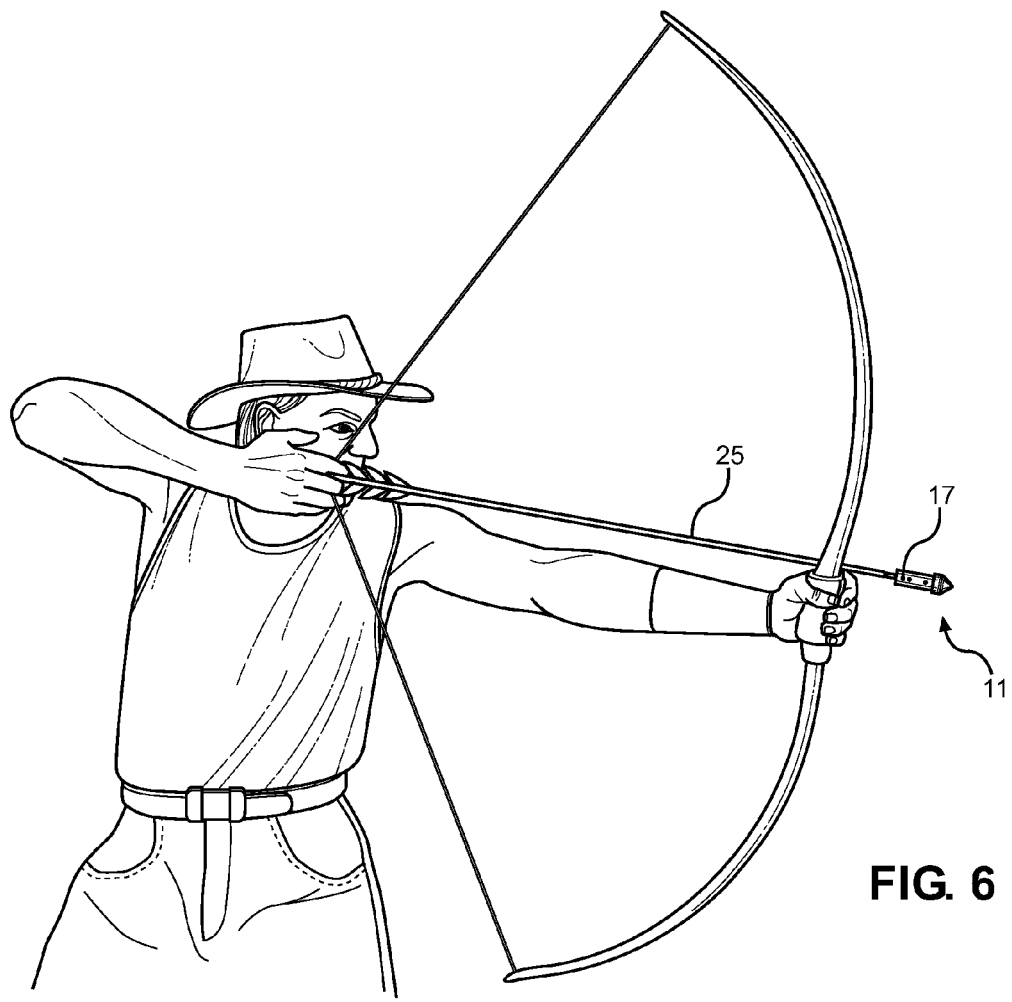
FIG. 6 shows a view of the scent-emitting arrowhead in use as disposed on the end of an arrow.

Referring now to FIG. 6, there is shown a view of the scent-emitting arrowhead in use as attached to an arrow. The scent-emitting arrowhead 11 is secured on the end of an arrow 25. The arrowhead has an aerodynamic shape so that the arrow can fly straight and can be shot with accuracy. The arrowhead has a small profile and is lightweight so that the arrowhead does not inhibit the ability of the arrow to be shot in the traditional manner. As the arrow flies through the air, the vents 17 disposed on the side of the arrowhead allow scent from the material deposited inside of the arrowhead to escape the container and emanate into the surroundings. Alternatively, the vents may allow the scented-material itself to be released into the surroundings. In this way, the arrowhead is able to disperse an animal attracting scent into the environment along its entire flight path.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A scent-emitting arrowhead, comprising:
   a container having a first end, an open second end, and an interior cavity that is adapted to hold a scented material;
   wherein said first end is adapted to attach to a shaft of an arrow;
   a lid removably secured to said second end of said container;
   a plurality of vents disposed along the container;
   wherein the vents are configured to allow the arrowhead to be oriented in a manner that prevents the scented material from being emitted from the interior cavity.

2. The scent-emitting arrowhead of claim 1, wherein said removable lid secures to said second end of said container by means of a snap connection.

3. The scent-emitting arrowhead of claim 1, wherein said removable lid is substantially conical in shape.

4. The scent-emitting arrowhead of claim 1, wherein said vents comprise circular apertures.

5. The scent-emitting arrowhead of claim 1, wherein said first end of said container comprises a threaded member that is adapted to attach to a shaft of an arrow.

6. The scent-emitting arrowhead of claim 1, wherein said plurality of vents are covered by one or more removable adhesive strips.

7. The scent-emitting arrowhead of claim 1, wherein said container is tubular.

8. The scent-emitting arrowhead of claim 1, wherein said removable lid comprises an O-ring such that a tight seal can be formed between said removable lid and said container.

9. The scent-emitting arrowhead of claim 1, wherein said plurality of vents are arranged in a line extending from said first end to said second end.

* * * * *